United States Patent [19]

Hofman et al.

[11] 4,272,515
[45] Jun. 9, 1981

[54] HAIR CONDITIONING SHAMPOO

[75] Inventors: Keith Hofman, Isleworth; Brian A. Scott, Leeds, both of England; Rudolf Vogl, Bad Segeberg, Fed. Rep. of Germany

[73] Assignee: Lever Brothers Company, New York, N.Y.

[21] Appl. No.: 807,110

[22] Filed: Jun. 16, 1977

[30] Foreign Application Priority Data

Jun. 21, 1976 [GB] United Kingdom ............... 25597/76

[51] Int. Cl.$^3$ ............................................... A61K 7/06
[52] U.S. Cl. ..................................... 424/70; 252/551
[58] Field of Search .......................... 424/70; 252/551

[56] References Cited

U.S. PATENT DOCUMENTS

| 3,580,853 | 5/1971 | Parran | 424/70 X |
| 3,816,616 | 6/1974 | Angvillo et al. | 424/70 |
| 3,958,581 | 5/1976 | Abegg et al. | 424/70 X |

Primary Examiner—Dale R. Ore
Attorney, Agent, or Firm—James J. Farrell; Melvin H. Kurtz; Irving N. Feit

[57] ABSTRACT

Hair conditioning shampoo comprising an alkyl ether sulphate detergent, 0.2 to 0.8% by weight of a cationic cellulosic resin as hair conditioning agent and, to increase the deposition of the resin on the hair during shampooing, an added amount of S% by weight of a water-soluble simple salt such that $(S/MW) \times N$ is from 0.03 to 0.21 where MW is the molecular weight of the salt and N is the number of ions produced by the salt in aqueous solution.

8 Claims, No Drawings

HAIR CONDITIONING SHAMPOO

This invention relates to shampoos.

It is well known to apply to the hair after shampooing a cream rinse conditioner product in order to make the hair more manageable, for example to make the hair easier to comb when wet.

More recently it has been proposed in U.S. Pat. No. 3,816,616 to obtain such conditioning effects also from a shampoo by including therein a Polymer JR resin which is a cellulosic cationic polymer, whose general formula, taken from U.S. Pat. No. 3,472,840, is referred to in the said patent. These Polymer JR resins are available commercially from the Union Carbide Corporation. There are a number of publications issued by the Union Carbide Corporation recommending shampoos based on anionic detergents in which the recommended amount of Polymer JR is 1.5% by weight of the shampoo. Indeed, some commercially marketed anionic-based shampoos employ this amount of Polymer JR. Such shampoos in use lead to the deposition of Polymer JR on to the hair in an amount sufficient to impart the desired conditioning effects.

However, the above shampoos are relatively expensive to produce, due to the cost of the cationic polymer, compared with conventional anionic-based shampoos.

It is an object of the present invention to produce a shampoo which is cheaper than the known conditioning shampoos referred to but which has a surprisingly high degree of effectiveness as a conditioning shampoo.

The invention is based on our discovery that for shampoos based on an alkyl ether sulphate anionic detergent and containing a Polymer JR resin a dramatic increase in the level of deposition can be obtained by the addition of S% by weight of a simple salt such that $(S/MW) \times N$ is from 0.03 to 0.21 where MW is the molecular weight of the salt and N is the number of ions produced by the salt in aqueous solution. This effect has not been obtained using other anionic detergents.

According to the present invention there is provided a hair conditioning shampoo comprising an aqueous solution containing A. 5% to 25% by weight of an alkyl ether sulphate detergent;

B. 0.2% to 0.8% by weight of a Polymer JR resin; and

C. an added amount S% by weight of a simple salt such that $(S/MW) \times N$ is from 0.03 to 0.21 where MW is the molecular weight of the salt and N is the number of ions produced by the salt in aqueous solution.

The alkyl ether sulphates are a known class of shampoo detergents. They have the general formula $R(OCH_2CH_2)_nOSO_3M$ where R is an alkyl group of 12 to 18 carbon atoms, M is a salt-forming cation and the average value of n is from 2 to 3. Particularly preferred is sodium lauryl ether sulphate but other salts such as the potassium and ammonium salts may also be used. The amount of the alkyl ether sulphate is preferably 10 to 20% by weight of the composition, the larger amounts of the detergent generally requiring the use of the higher levels of Polymer JR and/or the higher levels of salt to obtain comparable deposition of the polymer on to the hair during the shampooing operation.

The Polymer JR resins are the cellulosic cationic polymers having the following structural formula:

wherein $R_{cell}$ represents the residue of an anhydroglucose unit, Y is an integer of from 50 to 20,000 and wherein each R individually represents a substituent group of the following general formula:

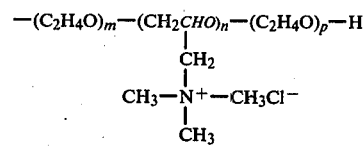

where m is a whole number of from 0 to 10, n is a whole number of from 0 to 3, and p is a whole number of from 0 to 10. The average values per anhydroglucose unit are: n from 0.35 to 0.45 and the sum of m+p is from 1 to 2. The polymers have molecular weights between about 100,000 and 3,000,000. The viscosity of the preferred cationic cellulose ethers is from 50 to 35,000 cps, measured according to ASTM D 2364-65 at 25° C. in a 2% by weight aqueous solution (Brookfield viscometer LVF, 30 rpm, spindle No. 2). Especially suitable are the cationic cellulosic derivatives sold by the Union Carbide Corporation under the trade names "JR 125", "JR 400" and "JR 30M" signifying a polymer of the type described having viscosities of 125 cps, 400 cps, and 30,000 cps, respectively.

By use of the present invention, shampoos having satisfactory hair conditioning properties can be formulated with the relatively small amount of 0.2 to 0.8% Polymer JR. Preferably the amount is about 0.4 to 0.6% giving a particularly good balance between effectiveness and raw material cost of the shampoo.

The third essential ingredient of the shampoo of the invention is the amount S% by weight of a simple salt such that $(S/MW) \times N$ is from 0.03 to 0.21 where MW is the molecular weight of the salt and N is the number of ions produced by the salt in aqueous solution. By a simple salt is meant a salt which dissolves in water and ionizes but whose ions do not aggregate in solution as, for example, do the ions of a surface active agent which aggregate to form micelles. Suitable salts include the water-soluble alkali metal, alkaline earth metal and ammonium salts (including substituted ammonium salts) of inorganic acids and organic acids containing a carbon chain of not more than about 6 carbon atoms. Chlorides, nitrates and sulphates are preferred inorganic salts and suitable salts of organic acids include the acetates and citrates. The molecular weight of the salt will usually be less than 600. Specific examples of suitable salts are sodium chloride, sodium nitrate, sodium sulphate, potassium chloride, ammonium chloride, calcium chloride, magnesium chloride, sodium acetate and sodium citrate.

The amount of salt referred to above is additional to any which may be present in the alkyl ether sulphate detergent.

The shampoo of the invention may contain one or more optional ingredients such as foam booster, preservative, colouring agent, perfume, opacifying agent. However, we have found that the Polymer JR has the effect of increasing the foaming power of the shampoo to such an extent that the inclusion of a conventional foam booster, such as a fatty acid amide, is not necessary. The pH of the shampoo is preferably from 5 to 7.5.

The invention will now be illustrated by reference to experiments carried out with various examples of shampoos in accordance with the invention and various other shampoos given for comparison purposes. All percentages are by weight.

EXAMPLE 1

An aqueous hair shampoo was formulated from the following ingredients:

|  | % |
|---|---|
| Sodium lauryl ether sulphate | 11.5 |
| Polymer JR 400 | 0.5 |
| Sodium chloride | 3.0 |
| Water, preservative | to 100.0 |
| pH from 6 to 7 | |

The sodium lauryl sulphate contained an average of 3 ethylene oxide units per molecule and was essentially free of salt.

Using a method of dye uptake for indicating the amount of the polymer deposited on hair when washed in a Polymer JR-containing shampoo, it was shown that from the above shampoo substantially the same amount of Polymer JR was deposited as from a similar shampoo containing the same amount of the detergent and the usual amount of 1.5% of Polymer JR 400 but no added sodium chloride.

This comparison was carried out by first shampooing and rinsing switches of blonde virgin hair taken from the same batch of hair with the shampoo containing 0.5% Polymer JR and sodium chloride, and with the shampoo containing 1.5% Polymer JR and no sodium chloride, respectively. Both groups of switches were then dyed with an aqueous solution of Pyrazole Fast Bordeaux 2BL and the L values of the coloured switches determined. The L value is a measure of the intensity of colour and hence of the degree of deposition on to the hair of the Polymer JR. The lower the L value, the greater the level of the deposition. The L value of the original untreated hair was also determined. The results are given in Table 1.

TABLE 1

| Polymer JR (%) | Sodium Chloride (%) | L value |
|---|---|---|
| 0.5 | 3.0 | 59.6 |
| 1.5 | 0 | 61.6 |
| untreated hair |  | 74.6 |

It was shown in various other experiments that simply washing hair switches in shampoo from which Polymer JR or both Polymer JR and sodium chloride had been omitted before applying the dye solution to the hair gave substantially the same L values as for the original untreated hair.

It should be explained that the intensity of the colouration produced by the dyestuff is measured in terms of the L co-ordinate value (reflectance) of the Adams Chromatic Value System as adapted by R. S. Hunter. L, a reflectance parameter, is related to Y, the well known chromaticity co-ordinate, by the expression: $L = 100\sqrt{Y}$. Y is defined in "Colour in Business, Science and Industry" by Judd and Wyszecki published by J. Wiley & Sons (1963). Spectral reflectance curves are measured on a Bausch and Lomb Spectronic 505 Ultraviolet spectrometer on chopped hair (in order to limit the specular components). The white reflectance substandard used is a clean titanium dioxide surface. Hunterlab values are calculated using the CIE 10° observer and CIE Standard Illuminant C. The derivation of the "Hunterlab" notation is fully described in ASTM Standards Part 21 (1965) published by the American Society for Testing and Materials at pages 270-273.

In a further series of experiments employing hair switches from the same batch but from a batch different from that used in the above experiments employing the shampoo of Example 1, a number of shampoos were made up according to the following formula:

|  | % |
|---|---|
| Sodium lauryl ether sulphate (as Example 1) | 11.5 |
| Polymer JR 400 | 0.2 or 0.8 |
| Sodium chloride | 0.1 or 6 |
| Water and preservative | to 100.0 |
| pH 6 to 7 | |

The deposition of Polymer JR on the hair during shampooing of the switches was again compared by treating the hair with the dye solution referred to in Example 1 and determining the L values for the various dyed switches. The results are given in Table 2.

TABLE 2

| Polymer JR (%) | Sodium Chloride (%) | L value |
|---|---|---|
| 0.2 | 0 | 64.2 |
| 0.2 | 1 | 61.5 |
| 0.2 | 6 | 60.9 |
| 0.8 | 0 | 61.5 |
| 0.8 | 1 | 57.1 |
| 0.8 | 6 | 57.0 |

For 1% and 6% sodium chloride the values of $(S/MW) \times N$, where S, MW and N have the above meanings, are 0.03 and 0.21, respectively.

These results show that inclusion of from 1% to 6% of sodium chloride in shampoos containing 0.2 to 0.8% of Polymer JR substantially increases the degree of deposition of the polymer on to the hair in the shampooing operation.

A number of other shampoos were formulated as in Example 1 save that the sodium chloride was replaced by another salt in an amount in the range 3 to 5% by weight of the composition. The other salts employed were sodium nitrate, sodium sulphate, sodium citrate, sodium acetate, potassium chloride, ammonium chloride, calcium chloride and magnesium chloride. For each added salt the respective value of $(S/MW) \times N$ was in the range 0.03 to 0.21. As before, the shampooed switches were treated with the dye solution to colour Polymer JR deposited on to the hair. The degree of dye uptake for each of these shampoos was visually compared with that from the corresponding shampoos which did not contain added salt. In each case the deposit of Polymer JR was shown to be increased by the addition of the salt and to be similar to that produced by the shampoo of Example 1.

In consumer tests the product of Example 1 and a comparative one containing 1.5% Polymer JR but no added salt were judged to give substantially the same hair conditioning effects and overall the product of the invention was preferred.

Thus the combined shampoo and cream rinse product of the invention in that it employs less Polymer JR than a conventional shampoo without loss of functionality is a cheaper product. Furthermore, the use of less Polymer JR can simplify the commercial manufacture of the shampoo.

In tests using formulae similar to that in Example 1 it was shown that the use of other anionic detergents gave unsatisfactory results. Other anionics tested included alkyl sulphates, succinates and alkyl benzene sulphonates. In such products the added salt either did not lead to any increase in Polymer JR deposition or else resulted in precipitation.

What is claimed is:

1. A hair conditioning shampoo consisting essentially of an aqueous solution of
   A. 5% to 25% by weight of an alkyl ether sulphate detergent;
   B. 0.2% to 0.8% by weight of cationic cellulosic resin having the general formula:

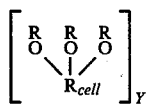

wherein
   $R_{cell}$ represents the residue of an anhydroglucose unit, Y is an integer of from 50 to 20,000 and wherein each R individually represents a substituent group of the following general formula:

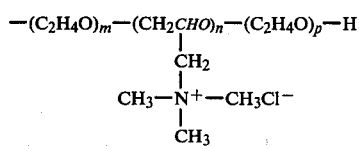

where
   m is a whole number of from 0 to 10, n is a whole number of from 0 to 3, and p is a whole number of from 0 to 10; and
   C. an added amount S% by weight of a simple salt such that $(S/MW) \times N$ is from 0.03 to 0.21 where MW is the molecular weight of the salt and N is the number of ions produced by the salt in aqueous solution.

2. A hair conditioning shampoo as claimed in claim 1 comprising 0.4 to 0.6% by weight of the cationic cellulosic resin.

3. A hair conditioning shampoo as claimed in claim 1, wherein the detergent is a sodium lauryl ether sulphate.

4. A hair conditioning shampoo as claimed in claim 1, wherein the salt is an alkali metal, alkaline earth metal or ammonium salt of an inorganic acid or an organic acid having a carbon chain of not more than 6 carbon atoms.

5. A hair conditioning shampoo as claimed in claim 4, wherein the salt is sodium chloride, sodium nitrate, sodium sulphate, sodium citrate, sodium acetate, potassium chloride, ammonium chloride, calcium chloride or magnesium chloride.

6. A hair conditioning shampoo as claimed in claim 1, wherein the amount of the salt is 3% to 5% by weight of the shampoo.

7. A hair conditioning shampoo as claimed in claim 1, wherein the salt is sodium chloride.

8. A hair conditioning shampoo as claimed in claim 1 consisting essentially of
   A. about 10% to about 20% by weight of an alkyl ether sulphate of the formula $R(OCH_2CH_2)_nOSO_3M$ where R is lauryl, M is a salt-forming cation selected from the group consisting of sodium, potassium and ammonium, and n has an average value of from about 2 to about 3;
   B. 0.2% to 0.8% by weight of cationic cellulosic resin having the general formula:

wherein
   $R_{cell}$ represents the residue of an anhydroglucose unit, Y is an integer of from 50 to 20,000 and wherein each R individually represents a substituent group of the following general formula:

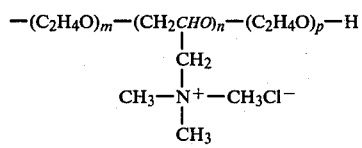

where
   m is a whole number of from 0 to 10, n is a whole number of from 0 to 3, and p is a whole number of from 0 to 10, said polymer in a 2% by weight aqueous solution having a viscosity of 50 to 35,000 centipoises at 25° C.; and
   C. an added amount S% by weight of a salt selected from the group consisting of alkali, alkaline earth and ammonium salts of inorganic acids and organic acids having a carbon chain of not more than 6 carbon atoms, said amount of the salt being such that $(S/MW) \times N$ is from 0.03 to 0.21 where MW is the molecular weight of the salt and N is the number of ions produced by the salt in aqueous solution.

* * * * *